United States Patent [19]

Patil et al.

[11] Patent Number: 5,599,530
[45] Date of Patent: Feb. 4, 1997

[54] SURFACE TREATED PIGMENTS

[75] Inventors: Anjali A. Patil, Westfield; Joseph F. Calello, Union; Robert W. Sandewicz, Spotswood, all of N.J.

[73] Assignee: Revlon Consumer Products Corporation, New York, N.Y.

[21] Appl. No.: 357,946

[22] Filed: Dec. 16, 1994

[51] Int. Cl.$^6$ .......................... A61K 7/043; A61K 7/027
[52] U.S. Cl. .......................... 424/63; 424/64; 424/78.03; 424/401; 434/100; 514/844; 106/447; 106/450; 106/493; 106/494
[58] Field of Search .................................. 106/493, 447, 106/494, 450; 424/401, 63, 64, 78.03; 434/100; 514/844

[56] References Cited

U.S. PATENT DOCUMENTS

| | | | |
|---|---|---|---|
| 2,978,347 | 4/1961 | Koehler | 106/450 |
| 4,606,914 | 8/1986 | Miyoshi | 424/63 |
| 4,622,074 | 11/1986 | Miyoshi | 106/419 |
| 4,755,229 | 7/1988 | Armanini | 106/413 |
| 4,832,944 | 5/1989 | Socci et al. | 106/447 |
| 4,837,011 | 6/1989 | Macchio | 424/69 |
| 4,882,133 | 11/1989 | Saegusa | 423/335 |
| 4,919,922 | 4/1990 | Miyoshi | 424/63 |
| 5,066,530 | 11/1991 | Kadokura | 428/98 |
| 5,068,056 | 11/1991 | Robb | 252/313.1 |
| 5,091,010 | 2/1992 | Souma | 106/403 |
| 5,091,013 | 2/1992 | Miyoshi | 106/505 |
| 5,167,709 | 12/1992 | Shinohara | 106/504 |
| 5,244,469 | 9/1993 | Shimoyama | 8/438 |
| 5,268,030 | 12/1993 | Floyd | 106/450 |
| 5,314,683 | 5/1994 | Schlossman | 424/63 |
| 5,482,547 | 1/1996 | Bugnon et al. | 106/493 |

FOREIGN PATENT DOCUMENTS 0306056  3/1989  European Pat. Off. .

OTHER PUBLICATIONS

Ken–React Reference Manual, Feb. 1985, Salvatore J. Monte, "Titanate, Zirconate and Aluminate Coupling Agents".

Royal Society of Chemistry Special Publication No. 76 "Additives for Water Based Coatings", Sep. 1988, D. Karsa, ed.

*Primary Examiner*—Mark L. Bell
*Assistant Examiner*—Scott L. Hertzog
*Attorney, Agent, or Firm*—Julie Blackburn

[57] ABSTRACT

An organic pigment particle having chemically bonded to its surface an organometallic zirconium compound, cosmetic compositions containing the pigment particles, and a method for reducing the staining potential of organic pigments.

19 Claims, No Drawings

SURFACE TREATED PIGMENTS

TECHNICAL FIELD

The invention is in the field of surface treated pigments and cosmetic compositions containing these pigments.

BACKGROUND OF THE INVENTION

Certified organic color additives are widely used in cosmetics, foods, and drugs, and are known as D&C (drug & cosmetic), and FD&C (food, drug & cosmetic) pigments. The D&C and FD&C colors are generally brighter, purer, and richer in color than their corresponding inorganic pigment counterparts. However, they are also more susceptible to degrading influences such as sunlight, chemical attack, and bleeding. In particular, pigment bleeding is problematic in cosmetics because it may cause staining of the lips, skin, and nails. Women who wear nail enamel are all too familiar with the stain that remains on the nails after removal of nail polish containing organic pigments. These stains are often difficult to remove and must simply wear away. Moreover, organic pigment staining is a particular problem with the new water based nail enamels which are being developed.

Various methods of treating organic pigments to prevent bleeding are known, including simply washing the pigment with water. New and improved ways to treat organic pigments to prevent bleeding are desirable.

SUMMARY OF THE INVENTION

The invention is directed to an organic pigment particle having an organometallic zirconium compound chemically bonded to its surface.

The invention is also directed to a cosmetic composition comprising:

0.01–85% of an organic pigment particle having an organo-metallic zirconium compound chemically bonded to its surface, 0.01–99 % of a cosmetically acceptable carrier.

The invention is also directed to a method for reducing the staining potential of organic pigments comprising chemically bonding to the surface of an organic pigment particle a organo-metallic zirconium compound.

SUMMARY OF THE INVENTION

The term "organo-metallic" means an organo-metallic compound wherein the metal has an oxidation state of one to eight. The organometallic compounds in accordance with the invention are derived from zirconium.

The term "chemically" means that the organo-metallic zirconium compound has free carboxyl and hydroxy groups which chemically bond to the free hydroxy, carboxyl, or metallic groups found on the pigment particle surface either covalently, or through hydrogen or ionic bonding.

Organo-metallic zirconium compounds suitable in accordance with the invention include:
cyclo[dineopentyl(diallyl)]pyrophosphato dineopentyl(diallyl) zirconate, cyclo(dioctyl)pyrophosphato dioctyl zirconate, cycloneopentyl cyclo(dimethylaminoethyl)pyrophosphate zirconate di mesyl salt, tetra (2,2 diallyloxymethyl)butyl di(ditridecyl)phosphito zirconate, neopentyl(diallyl)oxy trineodecanoyl zirconate, neopentyl(diallyl)oxy tri(dodecyl)benzene sulfonyl zirconate, neopentyl(diallyl)oxy tri(dioctyl)phosphato zirconate, neopentyl(diallyl)oxytri(dioctyl)pyrophsphato zirconate, neopentyl(diallyl)oxy tri(N-ethylenediamino) ethyl zirconate, neopentyl(diallyl)oxy tri-(m-amino)phenyl zirconate, neopentyl(diallyl)oxytrimethyacryl zirconate, neopentyl(diallyl)oxy triacryl zirconate, dineopentyl(diallyl)oxy diparamino benzoyl zirconate, dineopentyl(diallyl)oxy di(3-mercapto)propionic zirconate, 2,2-dimethyl 1,3 propanediolato bis(dioctyl)pyrophsphato-O (adduct) 2 moles N,N-dimethylamino-alkyl propenoamide zirconate, (2-ethyl, 2-propanolatomethyl) 1,3-propanediolato cyclo bis 2-dimethylamino pyrophosphato-O,O adduct with 2 moles of methanesulfonic acid zirconate, tetrakis 2,2(bis-2-propenolatomethyl)butanolato, adduct with 2 moles of ditridecyl hydrogen phosphite zirconate, 2-ethyl 2-propenolatomethyl 1,3-propanoediolato cyclo di 2,2-(bis-2-propenolatomethyl)butanolato pyrophosphato-O,O bis 2-ethylhexanolato cyclo (di-2-ethylhexyl)pyrophosphato zirconate, 2,2(bis-2-propenolatomethyl)butanolato tris neodecanoato-O zirconate, 2,2(bis-2-propenolatomethyl)butanolato tris (dodecyl)benzenesulfonato-O zirconate, 2,2 (bis-2-propenolatomethyl)butanolato tris (dioctyl)phosphato-O, 2,2(bis-2-propenolatomethyl)butanolato tris (dioctyl) phospato-O zirconate, 2,2(bis-2 -propenolatomethyl)butanolato tris 2 -methyl-2 -propenato-O zirconate, 2,2(bis-2-propenolatomethyl)butanolato tris 2-methyl-2-propenato-O zirconate, 2,2(bis-2propenolatomethyl)butanolato tris (dioctyl) pyrophospato-O zirconate, 2,2(bis-2-propenolatomethyl)butanolato pyrophosphato-O,O zirconate, 2,2(bis-2-propenolato butanolato tri 2-propenoato-O, 2,2(bis-2-propenolatomethyl)butanolato tri(2-ethylenediamino)ethylato zirconate, bis 2,2(bis-2-propenolatomethyl)butanolato bis (para amino benzoato-O) zirconate, bis 2,2(bis-2-propenolatomethyl)butanolato bis (3-mercapto) propionato-O zirconate, 1,1(bis-2-propenolatomethyl)butanolato tris (2-amino)phenylato zirconate, and mixtures thereof.

The term "organic pigment" means various aromatic types such as azo, indigoid, triphenylmethane, anthraquinone, hydroquinones and xanthine dyes, also referred to as the D&C and FD&C colors. These colors are set forth on page 21 of the *CTFA Cosmetic Ingredient Handbook*, First Edition, 1988, which is hereby incorporated by reference. Also included within this definition are the lakes of the D&C and FD&C colors, which consist generally of an insoluble metallic salt of a D&C and FD&C color deposited on an inert substrate such as alumina. The lakes are set forth on page 22 of the *CTFA Cosmetic Ingredient Handbook*, First Edition, 1988 which is also incorporated by reference herein.

The zirconium compounds are chemically bonded to the organic pigment surface by mixing the dry organic pigment with a mixture of a solvent, such as heptane. Any organic solvent is acceptable, so long as it is capable of facilitating the chemical bonding between the zirconium coupling agent and the pigment. The mixture is stirred well for 10 minutes to an hour. The solvent is then evaporated off by allowing the pigment to stand at room temperature. If desired, the treated pigment can be blended with surfactants prior to use.

The pigment particle of the invention generally comprises 0.1–90 %, more preferably 0.1–60% pigment and 0.01–90%, more preferably 0.1–80% organo-metallic zirconium compound, The term "cosmetically acceptable carrier" means a water or solvent based nail enamel or basecoat, or other color cosmetics where organic pigments are used such as lipsticks, blush, eyeshadow, makeup, mascara, and so on.

The pigments of the invention are particularly well suited for use in aqueous based nail enamel formulations as disclosed and claimed in copending patent application Ser. No. 357,005 filed Dec. 16, 1994, entitled "Aqueous Based Nail Enamel Compositions", by inventors Patil, et. al, filed on the same day as this application and hereby incorporated by reference. Suitable water based nail enamel compositions comprise:

0.01–40%, preferably 0.1–15%, more preferably 0.1–10% treated pigment, 0.01–75%, preferably 1–60%, more preferably 5–50% film former, and 0.01–85%, preferably 1–70%, more preferably 5–65% water.

Suitable film formers include synthetic polymers such as acrylate-methacrylate copolymers, acrylate polymers, styrene-acrylate copolymers, styrene-methacrylate copolymers, polyurethanes, polyesters, rosin esters, alkyd resins, polyvinylbutyral resin, polyamide, or mixtures thereof. The nail enamel composition may also contain thickeners, defoaming agents, rheology modifiers, preservatives, or mixtures of these ingredients. If present, 0.1–10% thickeners or rheology modifiers, are suggested, 0.01–5% defoaming agents, 0.1–30% coalescents, and 0.1–5% preservatives. Suitable thickeners are synthetic polymers such as acrylates or hydrophobically modified polyurethane thickening agents, as well as silica, montmorillonite minerals, acrylate thickeners, xanthan gum, guar gum, gum arabic, cellulose, cellulose derivatives, and mixtures thereof. Suitable defoaming agents include any nonionic, cationic, or anionic surfactant which acts by decreasing the tendency of the enamel to bubble. Coalescents are defined as ingredients capable of lowering the temperature at which a film forms. Suitable coalescents are glycol ethers, as well as other solvent-type compounds which will reduce the film forming temperature of the film former.

The pigments of the invention may also be incorporated into standard solvent-based nail enamels. Preferred are solvent based formulas comprising:

0.1–40% treated pigment,
0.1–80% organic solvent,
0.1–40% plasticizer,
0.1–40% film former.

The solvent should be innocuous to the user's nail and the other components of the nail enamel composition, should be capable of dissolving or dispersing the other components of the nail enamel to allow the components to flow onto the nail and should evaporate from the nail in a matter of minutes at room temperature and pressure. A variety of organic solvents fit into this category including $C_{1-10}$ acetates such as ethyl, butyl, propyl, isopropyl, and mixtures thereof, toluene, xylol, C1–10 alcohols such as ethyl, isopropyl, butyl, and so on, acetone, ketone derivatives, glycol ethers, aliphatic hydrocarbons, and mixtures thereof.

Plasticizers are substances will provide flexibility to the nail enamel film such that it will adhere to the nail and not readily chip or crack. Suitable plasticizers are the glyceryl triester compounds as described in U.S. Pat. No. 5,066,484 which is hereby incorporated by reference, as well as the more traditional phthalates, etc.

Film formers are defined as ingredients which are capable of forming a film on the nail which adheres to the degree necessary for commercial nail preparations. Suitable film formers include nitrocellulose, acrylics, polyurethanes, acrylates, vinyls, acrylonitrile/butadiene copolymers, styrene/butadiene copolymers, epoxies, and other polymers or copolymers such as those disclosed in U.S. Pat. No. 4,762, 703 which is hereby incorporated by reference.

The cosmetically acceptable carrier may also be a lipstick. Lipsticks generally contain 0.1–60% oil, 0.1–50% wax, and 0.1–40% pigment. Oils suitable for use in lipsticks are well known in the art, and include low viscosity surface oils having a viscosity of 5 to 2000 centipoise at 25° C. and are generally of the structure RCO-OR' wherein RCO represents a carboxylic acid radical and R is a $C_{1-25}$ straight or branched chain alkyl, and R' represents a straight or branched chain $C_{1-50}$ alkyl. Such oils include lanolin, vegetable oils, castor oil, other lanolin derivatives, triisocetyl citrate, sorbitan sesquioleate, ricinoleates, neopentanoate oils, and so on.

Suitable waxes or wax-like materials include those having a melt point of 35° to 120° C. Such waxes include polyethylene wax, synthetic wax, ceresin, paraffin, ozokerite, beeswax, carnauba, microcrystalline, organosilicon waxes, candelilla, polyolefins, shellac wax, whale, bayberry, or mixtures thereof.

The lipsticks of the invention may also contain preservatives, emulsifiers, antioxidants, and other ingredients.

The cosmetically acceptable carrier may be liquid makeup compositions such as those disclosed in U.S. Pat. No. 5,143,722, which is hereby incorporated by reference.

Other cosmetically acceptable carriers include blushes, eyeshadows, powdered cosmetics, and the like.

The invention will be further described in connection with the following examples which are set forth for the purpose of illustration only.

EXAMPLE 1

A beaker was filled with about 98 grams of D&C Red #6 barium lake. About 4 grams of cyclo[dineopentyl(diallyl)] pyrophosphato dineopentyl(diallyl)zirconate in a 50% w/w solution of heptane was added to the beaker. About 16 more grams of heptane was added to the beaker to wet out the pigment. The mixture was mixed well in a blender for about 10 minutes. The heptane was evaporated off by allowing the beaker to stand at room temperature overnight. Then, 35 grams of the treated pigment was blended with 9 grams of pigment wetting and dispersion grind aid Surfynol CT-131 and 56 grams 2,2,4-trimethyl 1,3 pentanediol monoisobutyrate. The pigment blend was then passed through a roller mill.

EXAMPLE 2

An aqueous nail enamel composition was made as follows:

|  | w/w % |
|---|---|
| Acrylic aqueous emulsion (46% solids)[1] | 61.1 |
| Aqueous polyurethane dispersion (35% solids)[2] | 24.1 |
| Coalescent[3] | 10.4 |
| Defoamer[4] | 0.4 |
| Pigment grind[5] | 4.0 |

[1] Polymethacrylate ester copolymer
[2] Anionic dispersion of aliphatic polyester urethane
[3] 2,2,4 trimethyl 1,3 pentanediol monoisobutyrate
[4] water based silicone elastomer
[5] 35.0 grams zirconated red #6, 9.0 grams Surfynol CT-131 (pigment wetting and dispersing agent), Air Products and Chemicals, 56.0 grams 2,2,4-trimethyl 1,3 pentanediol monoisobutyrate The nail enamel was applied to nails. Regular nail enamel remover was used to remove the enamel. After removal of enamel nails were substantially stain-free. The zirconium coupling agent used to treat D&C red #6 barium lake was Kenrich KZ-TPP zirconium IV 2-ethyl-2-propenolatomethyl 1-3-propandiolato, cyclo 2,2, (bis 2-propenolatomethyl) butanolato pyrophosphato 0-0,0.

While the invention has been described in connection with the preferred embodiment, it is not intended to limit the scope of the invention to the particular form set forth, but, ont he contrary, it is intended to cover such alternatives, modifications, and equivalents as may be included within the spirit and scope of the appended claims.

We claim:

1. A cosmetic composition comprising, by weight of the total composition:
   a) 0.01–99% of an organic pigment particle composition consisting essentially of an organic pigment particle and an organometallic zirconium compound wherein said organometallic zirconium compound is chemically bonded to the surface of the organic pigment particle, and
   b) 0.01–99% of a cosmetically acceptable carrier.

2. The composition of claim 1 wherein the organometallic zirconium compound is selected from the group consisting of:
   a) cyclo[dineopentyl(diallyl)pyrophosphato]dineopentyl-(diallyl)zirconate,
   b) cyclo(dioctyl)pyrophosphato dioctyl zirconate,
   c) cycloneopentyl cyclo(dimethylaminoethyl)pyrophosphate zirconium di mesyl salt,
   d) tetra(2,2 diallyloxymethyl)butyl di(ditridecyl)phosphito zirconate,
   e) neopentyl(diallyl)oxy trineodecanoyl zirconate,
   f) neopentyl(diallyl)oxy tri(dodecyl)benzene sulfonyl zirconate,
   g) neopentyl(diallyl)oxy tri(dioctyl)phosphato zirconate,
   h) neopentyl(diallyl)oxytri(dioctyl)pyrophospato zirconate,
   i) neopentyl(diallyl)oxy tri(N-ethylenediamino) ethyl zirconate,
   j) neopentyl(diallyl)oxy tri-(m-amino)phenyl zirconate,
   k) neopentyl(diallyl)oxy trimethylacryl zirconate,
   l) neopentyl(diallyl)oxy triacryl zirconate,
   m) dineopentyl(diallyl)oxy diparamino benzoyl zirconate,
   n) dinetopentyl(diallyl)oxy di(3-mercapto)propionic zirconate,
   o) 2,2-dimethyl 1,3 propanediolato bis(dioctyl)pyrophosphato-O (adduct) with 2 moles N,N-dimethylamino-alkyl propenoamide zirconate,
   p) (2-ethyl, 2-propanolatomethyl) 1,3-propanediolato cyclo bis 2-dimethylamino pyrophosphato-O,O adduct with 2 moles of methanesulfonc acid zirconate,
   q) tetrakis 2,2(bis-2-propenolatomethyl butanolato, adduct with 2 moles of ditridecyl hydrogen phosphite zirconate,
   r) 2-ethyl 2-propenolatomethyl 1,3-propanoediolato cyclo di 2,2-(bis-2-propenolatomethyl)butanolato pyrophosphato-O,O zirconate,
   s) bis 2-ethylhexanolato cyclo (di-2-ethylhexyl)pyrophosphato zirconate,
   t) 2,2(bis-2-propenolatomethyl)butanolato tris neodecanoato-O zirconate,
   u) 2,2(bis-2-propenolatomethyl) butanolato tris (dodecyl-)benzenesulfonato-O- zirconate,
   v) 2,2(bis-2-propenolatomethyl)butanolato tris(dioctyl)phosphato-O zirconate,
   w) 2,2(bis-2-propenolatomethyl) butanolato tris 2-methyl-2-propenato-O zirconate,
   x) 2,2(bis-2-propenolatomethyl)butanolato tris (dioctyl)pyrophosphato-O-zirconate,
   y) 2,2(bis-2-propenolatomethyl)butanolato pyrophosphato-O,O zirconate,
   z) 2,2(bis-2-propenolato) butanolato tri 2-propenoato-O zirconate,
   aa) 2,2(bis-2-propenolatomethyl) butanolato tri(2-ethylenediamino)ethylato zirconate,
   bb) bis 2,2(bis-2-propenolatomethyl)butanolato bis (para amino benzoato-O) zirconate,
   cc) bis 2,2(bis-2-propenolatomethyl)butanolato bis (3-mercapto)propionato-O zirconate,
   dd) 1,1(bis-2-propenolatomethyl)butanolato tris (2-amino)phenylato zirconate,
   ee) 2,2(bis-2-propenolatomethyl)butanolato zirconate, and
   ff) mixtures thereof.

3. The composition of claim 1 wherein the pigment particle is a D&C color, an FD&C color, a Lake of a D&C color, a Lake of an FD&C color, or mixtures thereof.

4. The composition of claim 3 which is a water based nail enamel comprising, by weight of the total composition:
   0.01–40% pigment particle composition,
   0.01–75% film former, and
   0.01–85% water.

5. The composition of claim 3 which is a solvent based nail enamel comprising:
   0.1–40% pigment particle composition,
   0.1–80% organic solvent,
   0.1–40% plasticizer,
   0.1–40% film former.

6. The composition of claim 3 which is a lipstick comprising:
   0.1–60% oil,
   0.1–50% wax, and
   0.1–40% pigment particle composition.

7. The composition of claim 4 wherein the film former is an acrylate copolymer acrylatemethacrylate copolymer, a styrene-acrylate copolymer, a styrene-methacrylate copolymer, and mixtures thereof.

8. The composition of claim 7 wherein the film former is an acrylate copolymer.

9. The composition of claim 8 comprising 0.1–10% rheology modifier.

10. The composition of claim 9 wherein the organometallic zirconium[dineapentyl(diallyl)]compound is cyclo pyrophosphato dineopentyl-(diallyl) zirconate.

11. The composition of claim 4 comprising:
    a) 0.1–15% of a pigment particle composition consisting essentially of an organic pigment particle selected from the group consisting of a D&C color, and FD&C color, a Lake of a D&C color, a Lake of an FD&C color, and mixtures thereof, and an organometallic zirconium compound selected from the group consisting of:
    a) cyclo dineopentyl(diallyl)zirconate,
    b) cyclo(dioctyl)pyrophosphato dioctyl zirconate,
    c) cycloneopentyl cyclo(dimethylaminoethyl)pyrophosphate zirconate di mesyl salt,
    d) tetra (2,2 diallyloxymethyl)butyl di(ditridecyl)phosphito zirconate,
    e) neopentyl(diallyl)oxy trineodecanoyl zirconate,
    f) neopentyl(diallyl)oxy tri(dodecyl)benzene sulfonyl zirconate,
    g) neopentyl(diallyl)oxy tri(dioctyl)phosphato zirconate,
    h) neopentyl(diallyl)oxytri(dioctyl)pyrophospato zirconate,
    i) neopentyl(diallyl)oxy ni(N-ethylenediamino) ethyl zirconate,
    j) neopentyl(diallyl)oxy tri-(m-amino)phenyl zirconate,
    k) neopentyl(diallyl)oxy trimethylacryl zirconate,
    l) neopentyl (diallyl)oxy triacryl zirconate,
    m) dineopentyl(diallyl)oxy diparamino benzoyl zirconate,
    n) dinetopentyl(diallyl)oxy di(3-mercapto)propionic zirconate, o) 2,2-dimethyl 1,3 propanediolato bis(dioctyl)pyrophosphato-O (adduct) with 2 moles N,N-dimethylamino-alkyl propenoamide zirconate,
p) (2-ethyl, 2-propanolatomethyl) 1,3-propanediolato cyclo bis 2-dimethylamino pyrophosphato-O,O adduct with 2 moles of methanesulfonc acid zirconate,
q) tetrakis 2,2(bis-2-propenolatomethyl butanolato, adduct with 2 moles of ditridecyl hydrogen phosphite zirconate,
r) 2-ethyl 2-propenolatomethyl 1,3-propanoediolato cyclo di 2,2-(bis-2-propenolatomethyl)butanolato pyrophosphato-O,O zirconate,
s) bis 2-ethylhexanolato cyclo (di-2-ethylhexyl)pyrophosphato zirconate,
t) 2,2(bis-2-propenolatomethyl)butanolato tris neodecanoato-O zirconate,
u) 2,2(bis-2-propenolatomethyl)butanolato tris (dodecyl)benzenesulfonato-O- zirconate,
v) 2,2(bis-2-propenolatomethyl)butanolato tris(dioctyl)phosphato-O zirconate,
w) 2,2(bis-2-propenolatomethyl)butanolato tris 2-methyl-2-propenato-O zirconate,
x) 2,2(bis-2-propenolatomethyl)butanolato tris (dioctyl)pyrophosphato-O-zirconate,
y) 2,2(bis-2-propenolatomethyl)butanolato pyrophosphato-O,O zirconate,
z) 2,2(bis-2-propenolato butanolato tri 2-propenoato-O zirconate,
aa) 2,2(bis-2 -propenolatomethyl) butanolato tri(2 -ethylenediamino)ethylato zirconate,
bb) bis 2,2(bis-2-propenolatomethyl)butanolato bis (para amino benzoato-O) zirconate,
cc) bis 2,2(bis-2-propenolatomethyl)butanolato bis (3-mercapto)propionato-O zirconate,
dd) 1,1(bis-2-propenolatomethyl)butanolato tris (2-amino)phenylato zirconate,
ee) 2,2(bis-2-propenolatomethyl)butanolato zirconate, and,
ff) mixtures thereof,
b) 5–50% of a film former selected from the group consisting of acrylate copolymers, acrylate-methacrylate copolymers, styrene-acrylate copolymers, and mixtures thereof,
c) 5–65% water.

12. The composition of claim 11 additionally comprising 0.1–10% by weight of the total composition of a thickener.

13. The composition of claim 12 additionally comprising 0.1–30% of a coalescent.

14. The composition of claim 5 wherein the organic solvent is selected from the group consisting of a $C_{1-10}$ alkyl acetate, toluene, xylol, $C_{1-10}$ alkyl alcohol, acetone, glycol ethers, aliphatic hydrocarbons, and mixtures thereof.

15. The composition of claim 5 wherein the film former is nitrocellulose.

16. The composition of claim 5 wherein the pigment particle composition consists essentially of a pigment particle selected from the group consisting of a D&C color, an FD&C color, a Lake of a D&C color, a Lake of an FD&C color, and mixtures thereof; and the organometallic zirconium compound is selected from the group consisting of:
a) cyclo dineopentyl(diallyl)zirconate,
b) cyclo(dioctyl)pyrophosphato dioctyl zirconate,
c) cycloneopentyl cyclo(dimethylaminoethyl)pyrophosphate zirconate di mesyl salt,
d) tetra (2,2 diallyloxymethyl)butyl di(ditridecyl)phosphito zirconate,
e) neopentyl(diallyl)oxy trineodecanoyl zirconate,
f) neopentyl(diallyl)oxy tri(dodecyl)benzene sulfonyl zirconate,
g) neopentyl(diallyl)oxy tri(dioctyl)phosphato zirconate,
h) neopentyl(diallyl)oxytri(dioctyl)pyrophospato zirconate,
i) neopentyl(diallyl)oxy tri(N-ethylenediamino) ethyl zirconate,
j) neopentyl(diallyl)oxy tri-(m-amino)phenyl zirconate,
k) neopentyl(diallyl)oxy trimethylacryl zirconate,
l) neopentyl (diallyl)oxy triacryl zirconate,
m) dineopentyl(diallyl)oxy diparamino benzoyl zirconate,
n) dinetopentyl(diallyl)oxy di(3-mercapto)propionic zirconate,
o) 2,2-dimethyl 1,3 propanediolato bis(dioctyl)pyrophosphato-O(adduct) with 2 moles N,N-dimethylamino-alkyl propenoamide zirconate,
p) (2-ethyl, 2-propanolatomethyl) 1,3-propanediolato cyclo bis 2-dimethylamino pyrophosphato-O,O adduct with 2 moles of methanesulfonc acid zirconate,
q) tetrakis 2,2(bis-2-propenolatomethyl butanolato, adduct with 2 moles of ditridecyl hydrogen phosphite zirconate.
r) 2-ethyl 2-propenolatomethyl 1,3-propanoediolato cyclo di 2,2-(bis-2-propenolatomethyl)butanolato pyrophosphato-O,O zirconate,
s) bis 2-ethylhexanolato cyclo (di-2-ethylhexyl)pyrophosphato zirconate,
t) 2,2(bis-2-propenolatomethyl)butanolato tris neodecanoato-O zirconate,
u) 2,2(bis-2-propenolatomethyl)butanolato tris (dodecyl)benzenesulfonato-O- zirconate,
v) 2,2(bis-2-propenolatomethyl)butanolato tris(dioctyl)phosphato-O zirconate,
w) 2,2(bis-2-propenolatomethyl)butanolato tris 2-methyl-2-propenato-O zirconate,
x) 2,2(bis-2-propenolatomethyl)butanolato tris (dioctyl)pyrophosphato-O-zirconate,
y) 2,2(bis-2-propenolatomethyl)butanolato pyrophosphato-O,O zirconate,
z) 2,2(bis-2-propenolato butanolato tri 2-propenoato-O zirconate,
aa) 2,2(bis-2-propenolatomethyl) butanolato tri(2-ethylenediamino)ethylato zirconate,
bb) bis 2,2(bis-2-propenolatomethyl)butanolato bis (para amino benzoato-O) zirconate,
cc) bis 2,2(bis-2-propenolatomethyl)butanolato bis (3-mercapto)propionato-O zirconate,
dd) 1,1(bis-2-propenolatomethyl)butanolato tris (2-amino)phenylato zirconate,
ee) 2,2(bis-2-propenolatomethyl)butanolato, and,
ff) mixtures thereof.

17. The composition of claim 6 wherein the pigment particle composition consists essentially of a D&C color, an FD&C color, a Lake of a D&C color, a Lake of an FD&C color, and mixtures thereof, and an organometallic zirconium compound selected from the group consisting of:
a) cyclo dineopentyl(diallyl)zirconate,
b) cyclo(dioctyl)pyrophosphato dioctyl zirconate,
c) cycloneopentyl cyclo(dimethylaminoethyl)pyrophosphate zirconate di mesyl salt,
d) tetra (2,2 diallyloxymethyl)butyl di(ditridecyl)phosphito zirconate,
e) neopentyl(diallyl)oxy trineodecanoyl zirconate,
f) neopentyl(diallyl)oxy tri(dodecyl)benzene sulfonyl zirconate,
g) neopentyl(diallyl)oxy tri(dioctyl)phosphato zirconate,
h) neopentyl(diallyl)oxytri(dioctyl)pyrophospato zirconate,
i) neopentyl(diallyl)oxy tri(N-ethylenediamino) ethyl zirconate,
j) neopentyl(diallyl)oxy tri-(m-amino)phenyl zirconate,
k) neopentyl(diallyl)oxy trimethylacryl zirconate, l) neopentyl (diallyl)oxy triacryl zirconate,
m) dineopentyl(diallyl)oxy diparamino benzoyl zirconate,
n) dinetopentyl(diallyl)oxy di(3-mercapto)propionic zirconate,
o) 2,2-dimethyl 1,3 propanediolato bis(dioctyl)pyrophosphato-O(adduct) with 2 moles N,N-dimethylamino-alkyl propenoamide zirconate,
p) (2-ethyl, 2-propanolatomethyl) 1,3-propanediolato cyclo bis 2-dimethylamino pyrophosphato-O,O adduct with 2 moles of methanesulfonc acid zirconate,
q) tetrakis 2,2(bis-2-propenolatomethyl butanolato, adduct with 2 moles of ditridecyl hydrogen phosphite zirconate,
r) 2-ethyl 2-propenolatomethyl 1,3-propanoediolato cyclo di 2,2-(bis-2-propenolatomethyl)butanolato pyrophosphato-O,O zirconate,
s) bis 2-ethylhexanolato cyclo (di-2-ethylhexyl)pyrophosphato zirconate,
t) 2,2(bis-2-propenolatomethyl)butanolato tris neodecanoato-O zirconate,
u) 2,2(bis-2-propenolatomethyl)butanolato tris (dodecyl)benzenesulfonato-O- zirconate,
v) 2,2(bis-2-propenolatomethyl)butanolato tris(dioctyl)phosphato-O zirconate,
w) 2,2(bis-2-propenolatomethyl)butanolato tris 2-methyl-2-propenato-O zirconate,
x) 2,2(bis-2-propenolatomethyl)butanolato tris (dioctyl)pyrophosphato-O-zirconate,
y) 2,2(bis-2-propenolatomethyl)butanolato pyrophosphato-O,O zirconate,
z) 2,2(bis-2-propenolato butanolato tri 2-propenoato-O zirconate,
aa) 2,2(bis-2-propenolatomethyl) butanolato tri(2-ethylenediamino)ethylato zirconate,
bb) bis 2,2(bis-2-propenolatomethyl)butanolato bis (para amino benzoato-O) zirconate,
cc) bis 2,2(bis-2-propenolatomethyl)butanolato bis (3-mercapto)propionato-O zirconate,
dd) 1,1(bis-2-propenolatomethyl)butanolato tris (2-amino)phenylato zirconate,
ee) 2,2(bis-2-propenolatomethyl)butanolato, and,
ff) mixtures thereof.

18. The composition of claim 17 wherein the oil has a viscosity of 5 to 2000 centipoise at 25° C.

19. The composition of claim 17 wherein the wax has a melting point of 35° to 120° C.

* * * * *